United States Patent [19]

Miyoshi et al.

[11] Patent Number: 5,693,503
[45] Date of Patent: Dec. 2, 1997

[54] PROCESS FOR PREPARATION OF AMINO ACID

[75] Inventors: Shinsuke Miyoshi; Hironori Kanamori; Manami Sato, all of Funabashi, Japan

[73] Assignee: Showa Sangyo Co., Ltd., Japan

[21] Appl. No.: 579,034

[22] Filed: Dec. 19, 1995

Related U.S. Application Data

[63] Continuation of Ser. No. 263,748, Jun. 22, 1994, abandoned, which is a continuation-in-part of Ser. No. 159,543, Dec. 1, 1993, abandoned.

[30] Foreign Application Priority Data

Dec. 3, 1992 [JP] Japan ............................ 4-350320

[51] Int. Cl.$^6$ ............................ C12P 13/24; C12P 13/04
[52] U.S. Cl. ............................ 435/107; 435/106; 435/910
[58] Field of Search ............................ 435/107, 106, 435/910

[56] References Cited

U.S. PATENT DOCUMENTS

| | | | |
|---|---|---|---|
| 4,224,409 | 9/1980 | Nakamori et al. | 435/107 |
| 4,444,885 | 4/1984 | Nakanishi et al. | 435/107 |
| 4,455,372 | 6/1984 | Chibata et al. | 435/107 |
| 5,364,775 | 11/1994 | Katsumata et al. | 435/107 |
| 5,374,542 | 12/1994 | Katsumata et al. | 435/107 |

*Primary Examiner*—Herbert J. Lilling
*Attorney, Agent, or Firm*—Nixon & Vanderhye

[57] ABSTRACT

This invention provides a process for preparation of trans-4-hydroxy-L-proline which comprises either culturing *Xanthomonas maltophilia* NA-62 (FERM BP-4479), *Xanthomonas maltophilia* JCM No.3807 (FERM BP-4474) or *Xanthomonas* sp. JCM No.3857 (FERM BP-4475) in a nutrient medium containing collagen or gelatin or a partial hydrolyzate of collagen or gelatin, or contacting culture cells of the above microorganism with collagen or gelatin or a partial hydrolyzate of collagen or gelatin in an aqueous medium, and recovering trans-4-hydroxy-L-proline formed; and a process for preparation of an amino acid mixture which comprises contacting culture cells, fractured cells before or after removal of the broken pieces of the cells, or a crude enzyme obtained by subjecting the fractured cells after removal of the broken pieces of the cells to salting-out or solvent precipitation, from *Xanthomonas maltophilia* NA-62 (FERM BP-4479), *Xanthomonas maltophilia* JCM No.3807 (FERM BP-4474) or *Xanthomonas* sp. JCM No.3857 (FERM BP-4475), with collagen or gelatin or a partial hydrolyzate of collagen or gelatin in an aqueous medium, and recovering the amino acid mixture formed. Trans-4-hydroxy-L-proline, and an amino acid mixture containing trans-4-hydroxy-L-proline and L-proline in a high concentration are efficiently produced by this invention.

4 Claims, No Drawings

PROCESS FOR PREPARATION OF AMINO ACID

CROSS REFERENCE TO RELATED APPLICATION

This is a continuation of application Ser. No. 08/263,748, filed Jun. 22, 1994, now abandoned, which is a continuation-in-part of Ser. No. 08/159,543, filed Dec. 1, 1993, now abandoned.

FIELD OF THE INVENTION AND RELATED ART STATEMENT

This invention relates to a process for preparing amino acid(s) from collagen or gelatin or a partial hydrolyzate of collagen or gelatin, specifically trans-4-hydroxy-L-proline or an amino acid mixture.

As proteins containing proline residues or hydroxyproline residues in abundance, collagen, casein, etc. originating in animals, and prolamine, etc. originating in vegetables have been known. These proteins are used as a raw material for production of a mixed amino acid solution by hydrolysis and/or production of specific amino acid(s) separated from the solution.

Chemical hydrolysis with an acid, an alkali or the like has exclusively been used to hydrolyze these protein materials. The reason is that peptides containing proline residues and/or hydroxyproline residues are hard to hydrolyze with general proteases, and often remain unhydrolyzed as hard to digest peptides (R. Walter, W. H. Simmons and T. Yoshimoto, Mol. Cell. Biochem., 30, 111, 1980), and their complete hydrolysis with enzymes has been considered to be substantially impossible.

It is reported that the severe reaction conditions in chemical hydrolysis bring about deterioration of the quality of amino acids produced, and moreover carcinogenic substances are produced during the reaction (M. R. Williams and M. F. Dutton, Joural of Food Protection, 51, 887, 1988). Therefore, the development of a process is needed whereby it is possible to hydrolyze such protein materials under more gentle conditions.

In recent years, several carboxypeptidases were found which act on the proline at the C-terminus of a peptide chain. For example, it is known (Kubota, et al., J. Biochem., 74, 757, 1973; Kubota et al., Protein•Nucleic Acid•Enzyme, 28, 1407, 1983) that carboxypeptidase $C_N$ and carboxypeptidase $C_U$ derived from citrus fruits grown in Japan such as natsumikan (summer mandarin) and unshumikan (unshu-mandarin) can release amino acids including proline which is especially resistant to hydrolysis by general proteases, as is the case with carboxypeptidase C (Nature, 201, 613, 1964) found by Zuber. However, the hydrolysis rates of these carboxypeptidases to release proline are very slow, and they are unsuitable for industrial application. A carboxypeptidase derived from a microorganism belonging to the genus Pycnoporus can also release the proline at the C-terminus of a peptide, but its action is not efficient (Japanese Published Unexamined Patent Application No. 201987/1983).

Carboxypeptidases such as carboxypeptidase P obtained from the culture broth of a miroooganism belonging to the genus Penicillium (Yokoyama, Protein•Nucleic Acid•Enzyme, 28, 1414, 1983) and carboxypeptidase Y derived from a baker's yeast (Hayashi, Protein•Nucleic Acid•Enzyme, 28, 1421, 1983) are also known. Both of them can fairly efficiently release proline at the C-terminus of a peptide, but the disadvantage that they do not easily act on the prolylproline bond of a peptide where proline exists in series.

Therefore, the carboxypeptidases so far known have been unsuited for industrially producing amino acids including hydroxyproline and proline from hard to digest proteins or peptides containing proline residues and/or hydroxyproline residues.

On the other hand, hydroxyproline and proline are particularly useful as raw materials for preparation of various pharmaceuticals. For example, hydroxyproline contained in hard to digest proteins or peptides containing proline residues and/or hydroxyproline residues is trans-4-hydroxy-L-proline and this is useful as a raw material for preparation of carbapenem antibiotics (Japanese Published Unexamined Patent Application No. 236980/1993).

However, a process for efficiently and selectively preparing hydroxyproline and/or proline by hydrolysis under mild conditions from hard to digest proteins or peptides has not hitherto been known.

Japanese Published Unexamined Patent Application No.236960/1993 published on Sep. 17, 1993 describes a carboxypeptidase capable of "catalyzing the hydrolysis of the prolyproline bond of peptides having proline in series" and a process for preparation thereof.

OBJECT AND SUMMARY OF THE INVENTION

An object of this invention is to provide a process for preparing trans-4-hydroxy-L-proline or an amino acid mixture by hydrolyzing collagen or gelatin or a partial hydrolyzate of collagen or gelatin, a hard to digest protein or peptide containing proline residues and/or hydroxyproline residues under mild conditions, without using an acid or alkali and severe reaction conditions.

Another object of this invention is to provide a process for preparing trans-4-hydroxy-L-proline or an amino acid mixture in high efficiency, by hydrolyzing collagen or gelatin or a partial hydrolyzate of collagen or gelatin, according to an enzyme method, namely by action of a microorganism or a treated product thereof (fractured cells or crude enzyme).

Another object of this invention is to provide a process for preparing trans-4-hydroxy-L-proline particularly useful as a raw material for preparation of carbapenem anitibiotics, etc. in high efficiency and selectively by hydrolyzing collagen or gelatin or a partial hydrolyzate of collagen or gelatin, according to an enzyme method.

These objects of this invention have been attained by a process for preparation of trans-4-hydroxy-L-proline which comprises either culturing Xanthomonas maltophilia NA-62 (FERM BP-4479), Xanthomonas maltophilia JCM No.3807 (FERM BP-4474) or Xanthomonas sp. JCM No.3857 (FERM BP-4475) in a nutrient medium containing collagen or gelatin or a partial hydrolyzate of collagen or gelatin, or contacting culture cells of the above microorganism with collagen or gelatin or a partial hydrolyzate of collagen or gelatin in an aqueous medium, and recovering trans-4-hydroxy-L-proline formed; and a process for preparation of an amino acid mixture which comprises contacting cuture cells, fractured cells before or after removal of the broken pieces of the cells, or a crude enzyme obtained by subjecting the fractured cells after removal of the broken pieces of the cells to salting-out or solvent precipitation, from Xanthomonas maltophilia NA-62 (FERM BP-4479), Xanthomonas maltophilia JCM No.3807 (FERM BP-4474)or Xanthomonas sp. JCM No.3857 (FERM BP-4475), with collagen or gelatin or a partial hydrolyzate of collagen or gelatin in an aqueous medium, and recovering the amino acid mixture formed.

DETAILED DESCRIPTION OF THE INVENTION

As to microorganisms used in the process of this invention, NA-62 is a private number, JCM is an abbreviation of Japan Collection of Microorganisms, and FERM BP means international deposit with National Institute of Bioscience and Human Technology, Agency of Industrial Science and Technology, the Ministry of International Trade and Industry, Japan, in accordance with the Budapest treaty on deposit of microorganisms. Microbial properties of the genus Xanthomonas and *Xanthomonas maltophilia* are disclosed in N. R. Krieg et al., "Bergey's Manual of Systematic Bacteriology", vol.1,WILLIAMS & WILKINS, Baltimore/ London, p140–219 (1984). *Xanthomonas maltophilia* NA-62 is the same strain as *Xanthomonas sp.* NA-62 disclosed in the Japanese Published Unexamined Patent Application No.236960/1993 mentioned above, and its microbial properties are disclosed therein. The NA-62 strain was identified to belong to *Xanthomonas maltophilia* since it has characteristics, in addition to the above microbial properties, that, as to its fatty acid composition, the cell contains branched fatty acids such as isopentadecanoic acid and isoheptadecanoic acid in a large amount and branched hydroxy fatty acids such as 3-hydroxyisoundecanoic acid and 3-hydroxy-isotridecanoic acid. In this connection, such fatty acid composition is considered to be characteristic of *Xanthomonas maltophilia* (see, for example, J. Swings, et al., Int. J. Syst. Bac., 33, 409, 1983; C. Wayne Moss et al., J. Bac., 114, 1018, 1973). Further, it was confirmed that the cell fatty acid composition was similar to that of a known microorganism, *Xanthomonas maltophilia* JCM No.1975.

The substrate used in this invention is collagen or gelatin or a partial hydrolyzate of collagen or gelatin. Collagen used in this invention is not particularly limited with its origin, but is usually derived from a mammal such as, for example, swine, cattle or equines. It is known that there are at least Types I to V as collagen of mammals (for example, the item of "collagen" in pages 480 to 481 of "Seikagaku Jiten" (Dictionary of Biochemistry), published by Tokyo Kagaku Dojin Co., Ltd.(1984)), and any type of collagen can be used in this invention. Commercial collagen can be used in this invention. Gelatin is modied collagen where the triple helical structure of collagen is destroyed (for example, the item of "gelatin" in page 700 of the above "Dictionary of Biochemistry"). Commercial gelatin can be used in this invention. The partial hydrolyzate of collagen or gelatin includes proteins and peptides (polypeptides and oligopeptides). According to literatures, proteins, polypeptides and oligopeptides have 50 or more, 10 to 50 and 2 to 10 amino acid residues, respectively (for example, the item of "peptide" in page 1141 of the above "Dictionary of Biochemistry"), and proteins and peptides are used in these senses in this invention. As the partial hydrolyzate of collagen or gelatin, either one obtained by chemical hydrolysis (e.g., acid hydrolysis) or one obtained using an enzyme such as collagenase can be used.

Production of trans-4-hydroxy-L-proline in this invention can be carried out by culturing a microorganism used in this invention, namely *Xanthomonas maltophilia* NA-62, *Xanthomonas maltophilia* JCM No.3807 or *Xanthomonas sp.* JCM No. 3857 in a medium containing collagen or gelatin or a partial hydrolyzate of collagen or gelatin (hereafter, "collagen or gelatin or a partial hydrolyzate of collagen or gelatin" is sometimes merely referred to as "collagen or the like") (hereafter, referred to as the first process).

Trans-4-hydroxy-L-proline is also produced by this invention by contacting microbial cells obtained by culturing a microoganism used in this invention in a conventional nutrient medium and them collecting the cells, with collagen or the like in an aqueous medium, and production of an amino acid mixture in this invention can be carried out by contacting the above microbial cells, fractured cells obtained by fracturing the microbial cells (any of those before or after removal of the broken pieces of the cells can be used), or a crude enzyme (comprising a mixture of enzymes) obtained by subjecting the fractured cells after removal of the broken pieces of the cells to salting-out or solvent precipitation, with collagen or the like in an aqueous medium (these processes are hereafter referred to as the second process).

First, description is made of the first process. A microorganism is cultured in a medium containing, moderately, carbon sources, nitrogen sources comprising mainly collagen or the like, inorganic matter, and micronutrients, under aerobic conditions, adjusting temperature, pH, etc.

Carbon sources usually used include various carbohydrates such as glucose, sucrose, mannose, starches, starch hydrolyzates and blackstrap molasses, but there can also be used, in accordance with assimilability, various organic acids such as pyruvic acid, fumaric acid, lactic acid and acetic acid, alcohols such as ethanol, glycerol and poyalcohol, hydrocarbons such as n-paraffin.

Nitrogen sources include collagen or gelatin or a partial hydrolyzate of collagen or gelatin, but other nitrogen sources can be used together therewith. Other nitogen sources include ammonia; various inorganic and organic ammonium salts such as ammonium chloride, ammonium sulfate, ammonium carbonate and ammonium acetate; urea and other nitrogen-containing compounds; and various nitrogen-containing natural products such as peptone, meat extract, yeast extract, corn steep liquor, casein hydrolyzates, fish meal or its digest, defatted soybean cake or its digest and chrysalis hydrolyzates. There is no particular limitation on the content of collagen or the like in all the nitrogen sources, but it is preferably 10 to 100 (w/w) %, particularly 50 to 100 (w/w) % on a dry basis.

Inorganic matter may include potassium primary phosphate, potassium secondary phosphate, magnesium sulfate, sodium chloride, ferrous sulfate, manganese sultate, calcium carbonate, etc. Although it is necessary to add to the medium suitable mounts of micronutrients (vitamins, nucleic acids, etc.) needed for growth of the microorganism used, these micronutrients may also be present in the natural products used as a nitrogen source.

Although it is usual to make collagen or the like exist in the total mount from the begining in the medium, it is also possible to intermittently add it or it is also possible to add the total mount during the culture (e.g., logarithmic phase). Although there is no particular limitation on the concentration of collagen or the like in the medium, it is usually determined in the range of 0.1 to 20 g/l.

It is optimal to carry out the culture using an aerobic culture method, for example a shaking culture method or an aeration stirring culture method, but it is also possible to appropriately combine a liquid standing culture method. As to culture conditions, generally the culture temperature is suitably 15° to 45° C., particularly 25° to 35° C. and the pH of the medium is suitably 5 to 8. The culture time is usually 10 hours to 10 days, preferably 24 hours to 6 days under these conditions. Using these procedures, it is possible to accumulate trans-4-hydroxy-L-proline mainly extracellularly.

Description is now made of the second process. First, a microorganism used in this invention is cultured in the same manner as in the first process. Although it is usual not to use collagen or the like as a nitrogen source in this embodiment of the invention, it is possible to use one.

When the microorganism is sufficiently proliferated, the culture is discontinued, the cells are separated by centrifugation, filtration or the like and, if necessary, washed, and the resultant cells or a treated product obtained by treating these cells are contacted with collagen or the like in an aqueous medium.

Treated products include fractured cells before or after removal of the broken pieces of the cells by centrifugation or the like, and a crude enzyme which was obtained from the fractured cells and has the ability to hydrolyze collagen or the like. Cells can be fractured using a conventional method, for example in a shaking type cell grinding machine, a high pressure cell destroying machine (Hughes press, French press or the like), an ultrasonic cell destroying machine or the like. The crude enzyme can be obtained by subjecting the fractured cells after removal of the broken pieces of the cells by centrifugation or the like, for example to salting-out using a salt containing a polyvalent anion such as a phosphate ion or a sulfate ion, for example ammonium sulfate, sodium sulfate, potassium phosphate or the like, particularly ammonium sulfate, or to solvent precipitation using ethanol, acetone, methanol, isopropanol or the like, or by recovering the resultant precipitate (crude enzyme) by centrifugation or the like and then desalting, decolorizing and/or deodorizing it. The "crude enzyme obtained by subjecting the fractured cells after removal of the broken pieces of the cells to salting-out or solvent precipitation" in this invention is assumed to include one subjected to the desalting, decolorizing and/or deodorizing operation(s).

The saturation degree of a salt in the case of salting-out can suitably be determined by gradually heightening the concentration of the salt, for example setting the first fractionation concentration at 20 to 30% saturation and then increasing it from there to 90 to 100% saturation with each 10 to 15% up, while the activity of the desired crude enzyme is used as an index. In the case of ammonium sulfate fractionation, for example, the proper saturation degree is 30 to 100% saturation, preferably 50 to 90% saturation. The saturation degree is expressed by a method where the concentration of a salt in a solution is expressed by weight %, and when the value is ½ of the salt concentration of the saturated solution, the saturation degree is defined as 50% saturation. In the salting-out, it is usually unnecessary to adjust temperature and pH, but it is also possible to adjust the temperature to a temperature of the order of 0° C. to room temperature and the pH to a pH of the order of 5 to 9.

The amount of a solvent to be added in the case of solvent precipitation can suitably be determined by gradually heightening the amount, while the activity of the desired crude enzyme is used as an index. In the case of ethanol, for example, the proper addition mount is on the order of 50 to 80% as (weight of solvent/(weight of an enzyme-containing solution+weight of solvent))×100. Preferably, solvent precipitation is carried out at 0° C. or less, for example at −30° to 0° C. In the solvent precipitation, it is usually unnecessary to adjust pH, but it is also possible to adjust the pH to a pH of the order of 5 to 9.

Desalting, decolorization and/or deodorization do not aim at separation among plural enzymes contained in the crude enzyme, but merely aim at desalting, decolorization and/or deodorization of the crude enzyme, and known methods therefor can widely be utilized. For example, desalting, decolorization and/or deodorization can be carried out by adsorption of colored matter and/or odorous matter using an anion exchange regin (particularly strongly basic anion exchange resin), an ion exchange cellulose, Sephadex or the like, ultrafiltration using an ultrafiltration membrane having a fractionation molecular weight of 10,000, dialysis, or the like.

Although it is advantageous to use a greater amount of the microbial cells or the treated product of the cells in the reaction, an excessive amount is economically disadvantageous. In general, when using microbial cells, a suitable amount is 0.1 to 100 mg of collagen or the like per mg of the cells (as dry cells), and in the case of the treated product of the cells, the amount used is generally 0.01 to 5 g of collagen or the like per unit enzyme activity (1 u). In this connection u denotes an enzyme activity sufficient to hydrolyze 1 μ mole of a substrate Z-Pro-Hyp at 37° C. for 1 minute. The concentration of collagen or the like is not particularly limited, but suitably is 0.01 to 20 g/dl.

The aqueous medium may be, for example, water, physiological saline, a buffer or the like. When fractured cells themselves are used as an enzymatic source, they already contain an aqueous medium and it is not always necessary to use an additional aqueous medium. Suitable buffers include phosphate buffers, succinate buffers, citrate buffers, Tris-HCl buffers, borate buffers, acetate buffers, glycylglycine buffers, etc.

The contact of the microbial cells or the treated product of the cells with collagen or the like in an aqueous medium is carried out, in general, at pH 5 to 8, at a temperature of 20° to 80° C., preferably 30° to 70° C. The contact time is usually 0.5 to 48 hours, particularly 0.5 to 24 hours. When the cells are used, they may die depending on temperature employed, but it causes no problem.

In either the first process or the second process, after completion of the reaction, the reaction is discontinued by a suitable means such as removal of the cells, inactivation of the enzyme with heating of the reaction mixture or inactivation of the enzyme with lowering of pH (addition of an acid such as hydrochloric acid); and membrane treatment using an ultrafiltration membrane or reverse osmosis filtration membrane or the like, adsorbent treatment using an adsorbent such as active carbon and other means known per se are used in an appropriate combination to obtain an amino acid mixed solution. When needed, it is possible to isolate a targeted specific amino acid (e.g., trans-4-hydroxy-L-proline) from the amino acid mixture using ion exchange chromatography, for example.

As demonstrated in later-described test examples, when the cells are used for production of amino acids in this invention, this invention is particularly advantageous for production of trans-4-hydroxy-L-Proline, and when the fractured cells or the crude enzyme are used, this invention is particularly advantageous for production of an amino acid mixture. This amino acid mixture is generally characterized in containing imino acids, namely trans-4-hydroxy-L-proline and L-proline in a high concentration.

All publications and patent applications cited in this specification are herein incorporated by reference as if each publication or patent application were specifically and individually indicated to be incorporated by reference.

This invention is specifically described below according to the following examples.

REFERENCE EXAMPLE 1

Each of three strains belonging to the genus Xanthomonas shown in Table 1 was inoculated in 100 ml of a liquid medium shown in Table 2 in a 500-ml conical flask equipped with a baffle, and cultured with shaking at 30° C. for 72 hours. After completion of the culture, the culture broth was centrifuged (15,000 rpm, 20 minutes), and the precipitate was collected as cells, and suspended in 4 ml of 50 mM bisTris-HCl buffer (pH6.5). The suspension was subjected to fracture of the cells using an ultrasonic homogenizer (US-150, produced by Nippon Seiki Seisaku-sho Co.). The broken cell pieces were removed from the resultant suspension by centrifugation (15,000 rpm, 15 minutes), the resultant supernatant was adjusted to 80% ammonium sulfate saturation, and the precipitate was collected as a crude protein by centrifugation (15,000 rpm, 20 minutes). The precipitate was suspended in 1 ml of 50 mM bisTris-HCl buffer (pH 6.5, containing 200 mM sodium chloride) to obtain a crude enzyme solution.

TEST EXAMPLE 1

Assay of synthetic peptide hydrolysis activity

A solution obtained by dissolving a commercial synthetic peptide Z-Pro-Hyp, Z-Pro-Pro or Z-Gly-Pro (Z: benzyloxycarbonyl group, Hyp: hydroxyproline) in 50 mM bisTris-HCl buffer (pH 6.5)to 1 mM concentration was used as a substrate solution. 25 µl of the crude enzyme solution obtained in Reference example 1 and 25 µl of 50 mM bisTris-HCl buffer (pH6.5 containing 200 mM sodium chloride) were added to 50 µl of this substrate solution, and the mixture was, after sufficient stirring, subjected to reaction at 37° C. for 60 minutes. 4 µl of 1N hydrochloric acid was added to stop the reaction.

The concentration of a free amino acid (proline or hydroxyproline) in the reaction solution was assayed using an automatic amino acid analyzer (Hitachi L-8500), the hydrolytic rate was calculated by comparing the resultant value with the concentration (theoretical value) of the (free) amino acid produced at the time of complete hydrolysis.

As a comparative example, 25 µl of a liquid obtained by suspending a commercial protease preparation "Actinase" (derived from *Streptomyces griseus* and produced by Kaken Pharmaceutical Co.) was added in place of the above crude enzyme solution (25,000,000 tyrosine units thereof was added per mmole of the synthetic peptide). This enzyme preparation has an extremely strong proteolytic power and is often used in proteolysis.

The results are shown in Table 3.

As apparent from Table 3, all of the crude enzyme solutions prepared from the three strains of the genus Xanthomonas used in this test exhibited hydrolytic activity of Z-Pro-Hyp and Z-Pro-Pro, and it was recognized that these strains have an ability to produce the enzyme. Further, hydrolytic activity of Z-Gly-Pro was observed in the crude enzyme solution prepared from *Xanthomonas maltophilia* JCM No.3807.

On the other hand, Actinase did not hydrolize any of the synthetic peptides.

TEST EXAMPLE 2

Assay of gelatin hydrolytic activity

Gelatin (produced by Wako Pure Chemical Industries, Ltd.) was dissolved in 50 mM bisTris-HCl buffer (pH 6.5) to prepare 0.5% (w/v) gelatin solution. 50 µl of the crude enzyme solution prepared in Reference example 1 was added to 50 µl of this gelatin solution, and the mixture was sufficiently stirred and subjected to reaction at 37° C. for 24 hours. Then, 4 µl of 1N hydrochloric acid was added to the reaction solution to stop the reaction. By assaying the free amino acid concentration in this reaction solution, gelatin hydrolytic activity, i.e. the amino acid releasing activity from gelatin, was assessed. The assay of free amino acid concentration was carried out using a phenylthiocarbamoyl (PTC)-amino acid analytical system (produced by Waters Co.). The results were expressed as a rate of a released amino acid to the amino acid (the case of hydrolysis with hydrochloric acid being assumed to be 100%) contained in the raw material gelatin.

As a comparative test, 50 µl of a liquid obtained by suspending Actinase in 50 mM bisTris-HCl buffer (pH 6.5, containing 200 mM sodium chloride)was added (100,000 tyrosine units thereof was added per g of gelatin).

The experimental results are shown in Table 4.

As apparent from Table 4, all of the crude enzyme solutions prepared from the microorganisms belonging to the genus Xanthomonas and used for this test exhibited high activity to form hydroxyproline and proline from gelatin. On the other hand, although formation of hydroxyproline and proline was observed in the case of Actinase, the amounts formed were comparatively much smaller.

TEST EXAMPLE 3

Production of amino acids by semi-fermentation

Xanthomonas sp. JCM No.3857 (FERM BP-4475) was cultured with shaking at 30° C. for 72 hours using a medium containing gelatin as the main nitrogen source shown in Table 5. After completion of the culture, the cells were removed by centrifugation (15,000 rpm, 20 minutes), the culture supernatant was treated with Sep Pak Cartridges (C18, produced by Waters Co.) to remove hydrophobic impurities, and the free amino acids concentrations were assayed using a PTC-amino acid analytic system (produced by Waters Co).

The test results are shown in Table 6.

As shown in Table 6, the free hydroxyproline content in the culture broth was 2.49 g/l, and 73.3% of the hydroxyproline contained in the protein in the medium was recovered as free hydroxyproline. Thus, it was possible to produce amino acids from gelatin by a semi-fermentation process using the microorganism, too.

TEST EXAMPLE 4

Production of amino acids by semi-fermentation

*Xanthomonas maltophilia* NA-62 (FERM BP-4479) was cultured with shaking at 30° C. for 72 hours using two liquid media (A and B) containing gelatin as the main nitrogen source shown in Table 9. After culture was complete, the cells were removed by centrifugation (15,000 rpm, 20 minutes), hydrophobic impurities were removed from the culture supernatant using Sep Pak Cartridges (C18, produced by Waters Co.), and the concentrations of the free amino acids were assayed using a PTC-amino acid analytical system (produced by Waters Co).

The test results are shown in Table 8 where the amount of each amino acid recovered from the culture broth is expressed as a recovery when hydrolysis with hydrochloric acid is assumed to be 100%. The content of hydroxyproline in the total amino acids in the culture broth is also shown.

As shown in Table 8, hydroxyproline is recovered by the semi-fermentation process using the microorganism not only with a high recovery but with a high content in the total amino acids. Thus, efficient preparation of hydroxyproline is provided by this invention.

TEST EXAMPLE 5

Production of amino acids by semi-fermentation

*Xanthomonas maltophilia* JCM No.3807 (FERM BP-4474) was cultured with shaking at 30° C. for 72 hours using a liquid medium containing gelatin as the main nitrogen source shown in Table 9. After completion of the culturing, the cells were removed by centrifugation (15,000 rpm, 20 minutes), hydrophobic impurities were removed from the culture supernatant using Sep Pak Cartridges (C18, produced by Waters Co.), and the concentrations of the free amino acids were assayed using a PTC-amino acid analytical system (produced by Waters Co).

The test results are shown in Table 10 where the amount of each amino acid recovered from the culture broth is expressed as a recovery when the hydrolysis with hydrochloric acid is assumed to be 100%. The content of hydroxyproline in the total amino acids in the culture broth is also shown.

As shown in Table 10, hydroxyproline is recovered by the semi-fermentation process using the microorganism not only in a high recovery but with a high content thereof in the total amino acids. Thus, efficient preparation of hydroxyproline is provided by this invention.

REFERENCE EXAMPLE 2

Preparation of a cell suspension

Each of three strains, *Xanthomonas maltophilia* NA-62 (FERM BP-4479), *Xanthomonas maltophilia* JCM No.3807 (FERM BP-4474) and *Xanthomonas* sp. JCM No.3857 (FERM BP-4475) was inoculated in 100 ml of a liquid medium shown in Table 2 in a 500-ml conical flask equipped with a baffle, and cultured with shaking at 30° C. for 72 hours. After completion of the culture, the culture broth was centrifuged (15,000 rpm, 20 minutes), and the precipitate was collected as cells. The cells were suspended in physiological saline (0.9% aqueous sodium chloride solution), and the suspension was centrifuged (15,000 rpm, 10 minutes) to collect cells (washing). This operation was made twice, and the cells collected were suspended in 10 ml of physiolgical saline to give a cell suspension.

REFERENCE EXAMPLE 3

Preparation of a cell fracture extract

Each of three strains, *Xanthomonas maltophilia* NA-62 (FERM BP-4479), *Xanthomonas maltophilia* JCM No.3807 (FERM BP-4474) and *Xanthomonas* sp. JCM No.3857 (FERM BP-4475) was inoculated in 100 ml of a liquid medium shown in Table 2 in a 500-ml conical flask equipped with a baffle, and cultured with shaking at 30° C. for 72 hours. After completion of the culture, the culture broth was centrifuged (15,000 rpm, 20 minutes), and the precipitate was collected as cells. The cells were suspended in 15 ml of 50 mM bisTris-HCl buffer (pH 6.5), and fractured using an ultrasonic homogenizer (US-150, produced by Nippon Seiki Seisaku-sho Co.). The broken pieces of the cells were removed from this suspension by centrifugation (15,000 rpm, 15 minutes) to give a cell fracture extract.

TEST EXAMPLE 6

Test of hydrolysis of gelatin

Gelatin (produced by Wako Pure Chemical Industries, Ltd.) was dissolved in 50 mM bisTris-HCl buffer (pH 6.5) to prepare 5% (w/v) gelatin solution. 3,800 μl each of the cell suspension and the cell fracture extract prepared by above procedures were added to 200 μl portions of this gelatin solution, respectively (about 1 mg of gelatin per mg of the cells (as dry cells) and 0.14 to 0.2 g of gelatin per unit enzyme activity (1 u)).

Each of the mixtures was sufficiently stirred and then subjected to reaction at 50° C. for 24 hours. 160 μl of 1N hydrochloric acid was added to the reaction mixture to stop the reaction. The free amino acids in this reaction mixture were assayed in the same manner as in Test example 2.

The test results are shown in Table 11. The meaning of % in the table is the same as in Test example 2. As apparent from Table 11, all of the cell suspensions and the cell fracture extract prepared from the microorganisms belonging to the genus Xanthomonas used in this test exhibited high activity to form amino acids including hydroxyproline and proline from gelatin.

TABLE 1

| Microorganisms on which tests were made | |
|---|---|
| Name of strain | No. |
| *Xanthomonas maltophilia* NA - 62 | FERM BP - 4479 |
| *Xanthomonas maltophilia* | JCM No. 3807 (FERM BP - 4474) |
| *Xanthomonas* sp. | JCM No. 3857 (FERM BP - 4475) |

TABLE 2

| Composition of liquid medium | |
|---|---|
| Meat extract | 5 (g/l) |
| Peptone | 10 |
| Yeast extract | 3 |
| Sodium chloride | 3 |
| Glucose | 10 |
| Potassium primary phosphate | 3 |
| Magnesium sulfate heptahydrate | 5 |
| pH | 7.2 |

TABLE 3

| Hydrolytic activity on synthesized peptide | | | |
|---|---|---|---|
| | Hydrolytic rate (%) | | |
| | Z—Pro—Pro | Z—Pro—Hyp | Z—Gly—Pro |
| *Xanthomonas maltophilia* NA - 62 | 41.8 | 30.2 | 0 |
| *Xanthomonas maltophilia* | 29.5 | 24.5 | 34.4 |
| *Xanthomonas* sp. | 49.3 | 32.9 | 0 |
| Actinase (comparative example) | 0 | 0 | 0 |

TABLE 4

Amino acid releasing activity from gelatin

| | Hyp | Pro | Asp | Glu | Ser | Gly | Arg | Thr | Ala | Val | Ile | Leu | Phe | Lys |
|---|---|---|---|---|---|---|---|---|---|---|---|---|---|---|
| *Xanthomonas maltophilia* NA-62 | 83 | 36 | 30 | 72 | 100 | 68 | 80 | 0 | 100 | 80 | 100 | 0 | 87 | 100 |
| *Xanthomonas maltophilia* | 33 | 52 | 0 | 10 | 100 | 58 | 60 | 0 | 100 | 20 | 0 | 100 | 16 | 100 |
| *Xanthomonas sp.* | 65 | 100 | 13 | 91 | 97 | 88 | 100 | 100 | 100 | 100 | 100 | 100 | 87 | 100 |
| Actinase | 7 | 4 | 18 | 23 | 46 | 23 | 49 | 100 | 60 | 92 | 47 | 57 | 56 | 66 |

TABLE 5

Composition of liquid medium

| | |
|---|---|
| Meat extract | 5 (g/l) |
| Gelatin | 50 |
| Yeast extract | 5 |
| Sodium chloride | 3 |
| Glucose | 10 |
| Potassium primary phosphate | 3 |
| Magnesium sulfate heptahydrate | 5 |
| pH | 7.2 |

TABLE 6

Gelatin hydrolysis activity in semi-fermentation

| Amino acid | Production amount (g/l) | Recovery (%) |
|---|---|---|
| Hydroxyproline | 2.49 | 73.3 |
| Aspartic acid | 0.35 | 14.8 |
| Glutamic acid | 0.41 | 8.7 |
| Serine | 0.34 | 23.0 |
| Glycine | 4.68 | 52.8 |
| Histidine | 0.20 | 58.0 |
| Arginine | 2.50 | 70.3 |
| Threonine | 0.14 | 18.6 |
| Alanine | 0.22 | 6.1 |
| Proline | 0.20 | 3.7 |
| Tyrosine | 0.38 | 100 |
| Valine | 0.08 | 7.4 |
| Methionine | 0.14 | 5.6 |
| Isoleucine | 0.14 | 22.2 |
| Leucine | 0.06 | 4.9 |
| Phenylalanine | 0.24 | 16.0 |
| Lysine | 0.03 | 2.0 |

TABLE 7

Composition of liquid medium

| | Medium A | Medium B |
|---|---|---|
| Meat extract | 5 (g/l) | — (g/l) |
| Gelatin | 10 | 10 |
| Yeast extract | 5 | — |
| Sodium chloride | 3 | — |
| Glucose | 10 | — |
| Potassium primary phosphate | 3 | 25 |
| Magnesium sulfate heptahydrate | 5 | — |
| Sodium carbonate | — | 0.5 |
| Sodium sulfate | — | 0.114 |
| Magnesium chloride monohydrate | — | 0.163 |
| Ferric chloride | — | 0.001 |
| Zinc chloride | — | 0.007 |
| Calcium chloride dihydrate | — | 0.012 |
| Citric acid | — | 2.3 |
| Boric acid | — | 0.006 |
| pH | 7.2 | 7.2 |

TABLE 8

Hydrolysis of gelatin by semi-fermentation

| Released amino acid | Medium A | Medium B |
|---|---|---|
| Hydroxyproline | 99 (%) | 72 (%) |
| Aspartic acid | 8 | 9 |
| Glutamic acid | 3 | 1 |
| Serine | — | trace |
| Glycine | — | trace |
| Histidine | — | — |
| Arginine | 3 | 1 |
| Threonine | 8 | 8 |
| Alanine | 3 | — |
| Proline | — | — |
| Tyrosine | trace | — |
| Valine | trace | — |
| Methionine | — | trace |
| Isoleucine | — | 3 |
| Leucine | — | — |
| Phenylalanine | 27 | — |
| Lysine | trace | — |
| Content (%) of hydroxyproline on all the amino acids | 76 | 87 |

Recovery of each amino acid was calculated assuming the value by hydrochloric acid hydrolysis to be 100%.
trace: Although presence in a very small amount was detected, quanititative determination was impossible.
—: not detected

TABLE 9

Composition of liquid medium

| | |
|---|---|
| Meat extract | 5 (g/l) |
| Gelatin | 10 |
| Yeast extract | 5 |
| Sodium chloride | 3 |
| Glucose | 10 |
| Potassium primary phosphate | 3 |
| Magnesium sulfate heptahydrate | 5 |
| pH | 7.2 |

TABLE 10

Hydrolysis of gelatin by semi-fermentation

| Released amino acid | Recovery |
|---|---|
| Hydroxyproline | 86 (%) |
| Aspartic acid | 8 |
| Glutamic acid | 2 |
| Serine | — |
| Glycine | — |
| Histidine | 20 |
| Arginine | 3 |
| Threonine | — |
| Alanine | 1 |
| Proline | — |

TABLE 10-continued

| Hydrolysis of gelatin by semi-fermentation | |
|---|---|
| Released amino acid | Recovery |
| Tyrosine | 3 |
| Valine | — |
| Methionine | — |
| Isoleucine | 3 |
| Leucine | — |
| Phenylalanine | 15 |
| Lysine | 1 |
| Content (%) of hydroxyproline on all the amino acids | 81 |

Recovery of each amino acid was calculated assuming the value by hydrochloric acid hydrolysis to be 100%.
—: not detected

TABLE 11

Amino acid releasing activity from gelatin

%

| | Hyp | Pro | Asp | Glu | Ser | Gly | Arg | Thr | Ala | Va | Ile | Leu | Phe | Lys |
|---|---|---|---|---|---|---|---|---|---|---|---|---|---|---|
| Cell suspension | | | | | | | | | | | | | | |
| NA-62 | 76 | 72 | 27 | 51 | 54 | 75 | 13 | 59 | 100 | 100 | 69 | 100 | 100 | 78 |
| JCM 3807 | 78 | 68 | 7 | 2 | 0 | 61 | 0 | 0 | 74 | 60 | 28 | 50 | 30 | 0 |
| JCM 3857 | 75 | 74 | 0 | 14 | 0 | 86 | 0 | 83 | 100 | 100 | 48 | 96 | 53 | 80 |
| Cell fracture extract | | | | | | | | | | | | | | |
| NA-62 | 36 | 30 | 5 | 43 | 54 | 56 | 35 | 53 | 72 | 49 | 15 | 30 | 68 | 31 |
| JCM 3807 | 40 | 32 | 50 | 67 | 71 | 52 | 47 | 100 | 94 | 97 | 54 | 78 | 53 | 9 |
| JCM 3857 | 81 | 63 | 75 | 100 | 55 | 85 | 66 | 100 | 100 | 100 | 67 | 100 | 100 | 100 |

What is claimed is:

1. A process for preparation of trans-4-hydroxy-L-proline which comprises either culturing Xanthomonas maltophilia NA-62 (FERM BP-4479), Xanthomonas maltophilia JCM No.3807 (FERM BP-4474) or Xanthomonas sp. JCM No.3857 (FERM BP-4475) in a nutrient medium containing collagen or gelatin or a partial hydrolyzate of collagen or gelatin, or contacting culture cells of the above microorganism with collagen or gelatin or a partial hydrolyzate of collagen or gelatin in an aqueous medium, and recovering trans-4-hydroxy-L-proline formed.

2. A process for preparation of trans-4-hydroxy-L-proline which comprises either culturing Xanthomonas maltophilia NA-62 (FERM BP-4479), Xanthomonas maltophilia JCM No.3807 (FERM BP-4474) or Xanthomonas sp. JCM No.3857 (FERM BP-4475) in a nutrient medium containing collagen or gelatin, or contacting culture cells of the above microorganism with collagen or gelatin in an aqueous medium, and recovering trans-4-hydroxy-L-proline formed.

3. A process for preparation of an amino acid mixture which comprises contacting culture cells, fractured cells before or after removal of the broken pieces of the cells, or a crude enzyme obtained by subjecting the fractured cells after removal of the broken pieces of the cells to salting-out or solvent precipitation, from Xanthomonas maltophilia NA-62 (FERM BP-4479), Xanthomonas maltophilia JCM No.3807 (FERM BP-4474) or Xanthomonas sp. JCM No.3857 (FERM BP-4475), with collagen or gelatin or a partial hydrolyzate of collagen or gelatin in an aqueous medium, and recovering the amino acid mixture formed.

4. A process for preparation of an amino acid mixture which comprises contacting culture cells, fractured cells before or after removal of the broken pieces of the cells, or a crude enzyme obtained by subjecting the fractured cells after removal of the broken pieces of the cells to salting-out or solvent precipitation, from Xanthomonas maltophilia NA-62 (FERM BP-4479), Xanthomonas maltophilia JCM No.3807 (FERM BP-4474) or Xanthomonas sp. JCM No.3857 (FERM BP-4475), with collagen or gelatin in an aqueous medium, and recovering the amino acid mixture formed.

* * * * *